United States Patent
Gonzalez-Martin et al.

(10) Patent No.: US 6,994,777 B2
(45) Date of Patent: Feb. 7, 2006

(54) CHEMICAL SENSORS UTILIZING CONDUCTING POLYMER COMPOSITIONS

(75) Inventors: Anuncia Gonzalez-Martin, San Jose, CA (US); Jinseong Kim, College Station, TX (US); Harry Jabs, College Station, TX (US); Armando Solar, College Station, TX (US); Larris Andrew Rutherford, Jr., College Station, TX (US); Daniel Westerheim, College Station, TX (US)

(73) Assignee: Lynntech, Inc., College Station, TX (US)

(*) Notice: Subject to any disclaimer, the term of this patent is extended or adjusted under 35 U.S.C. 154(b) by 105 days.

(21) Appl. No.: 10/234,980

(22) Filed: Sep. 4, 2002

(65) Prior Publication Data

US 2004/0040841 A1   Mar. 4, 2004

(51) Int. Cl.
*G01N 27/26* (2006.01)

(52) U.S. Cl. .............. 204/406; 204/421; 204/230.8
(58) Field of Classification Search .......... 204/406, 204/416, 418, 422, 424; 205/787; 422/82.02, 422/98; 436/150
See application file for complete search history.

(56) References Cited

U.S. PATENT DOCUMENTS

| | | | |
|---|---|---|---|
| 4,086,541 A | * | 4/1978 | Katou et al. ............ 330/51 |
| 4,992,724 A | * | 2/1991 | Hisanaga et al. ......... 323/367 |
| 5,571,401 A | * | 11/1996 | Lewis et al. ............ 205/787 |
| 5,674,752 A | | 10/1997 | Buckley et al. |
| 5,675,070 A | | 10/1997 | Gelperin |
| 5,756,879 A | * | 5/1998 | Yamagishi et al. ....... 73/28.01 |
| 5,918,257 A | | 6/1999 | Mifsud et al. |
| 6,033,630 A | | 3/2000 | Hinton et al. |
| 6,093,308 A | | 7/2000 | Lewis et al. |
| 6,137,708 A | | 10/2000 | Lin et al. |
| 6,290,911 B1 | | 9/2001 | Lewis et al. |

FOREIGN PATENT DOCUMENTS

JP    58-076771 A  *  5/1983

* cited by examiner

*Primary Examiner*—Roy King
*Assistant Examiner*—Harry D. Wilkins, III
(74) *Attorney, Agent, or Firm*—Streets & Steele; Frank J. Campigotto; Jeffrey L. Streets

(57) ABSTRACT

A chemical sensor for detecting the presence of one or more analytes. The sensor comprises at least one electrode pair and a photopolymerized electrically conducting polymer composition disposed in contact between each of the electrode pairs. Each polymer composition may include an organic polymer capable of interacting with one or more analytes. The sensor also comprises a means for delivering an analyte to each polymer composition, and a means for processing the resultant electronic signal from each polymer composition and electrode pair. Preferably, the sensor comprises a plurality of different polymer compositions, each with a dedicated electrode pair, to generate a collection of signals that provide a fingerprint unique to a particular analyte.

39 Claims, 7 Drawing Sheets

CHEMICAL SENSORS UTILIZING CONDUCTING POLYMER COMPOSITIONS

BACKGROUND OF THE INVENTION

This invention was made with government support under grant number DMI-9761605 awarded by the National Science Foundation (NSF). The government has certain rights in this invention.

FIELD OF THE INVENTION

The present invention relates to electronic sensors for sensing and identifying chemical vapors, as well as formulations and methods for preparation and use thereof.

BACKGROUND OF THE RELATED ART

A conventional approach to chemical sensors is based on the precise chemical design of the receptor site, known as a "lock-and-key" design, where a specific receptor is synthesized to selectively bind the analyte of interest. This approach is apt when a specific analyte is to be identified in the presence of controlled backgrounds. However, such an approach requires the synthesis of a single, highly selective sensor for each and every analyte. An alternative chemical sensing method is conceptually closer to the design proposed for the mammalian sense of olfaction, where the "lock-and-key" approach is replaced by a more combinatorial approach. There, an array of incrementally different sensor elements is used, where every element is chosen to respond to a variety of chemicals. For the array to respond to the largest possible number of analytes, the elements of the array should contain as much chemical diversity as possible. An array of such sensing elements will produce a chemically reversible diagnostic signal, such as a change in electrical resistance, upon exposure to different analytes. In this approach, identification of an analyte will not typically be accomplished from the response of a single sensor element. Instead, the identification and quantification of an analyte will be accomplished by a distinct pattern of responses produced over the sensor elements in the array. Ideally, an array sensor would solve the critical problem of how to incorporate into a single system both selectivity for many chemicals and high sensitivity, where distinctive molecular signatures of a compound are encoded by cross-reactive receptor elements, in conjunction with a pattern recognition method.

Most existing arrays of chemical sensors have been used in the identification of vapor mixtures of organic compounds, odors and aromas. Attempts to produce a broadly responsive sensor array have used such technologies as heated metal oxide thin film resistors, metal-oxide-silicon field-effect-transistors (MOSFETs), polymer sorption layers on the surface of acoustic wave (SAW) resonators, piezoelectric thickness-shear-mode (TSM) acoustic wave sensors, electrochemical detectors, carbon black-organic polymer composites, conducting polymers, and fiber optics. Arrays of metal oxide thin film resistors, typically based on $SnO_2$ films coated with various catalysts, produce responses for several analytes. However, the $SnO_2$ arrays do not produce reproducible responses from array to array. Also, such arrays are susceptible to poisoning by sulfur-containing compounds and weak acids, and require high power consumption for heating elements. MOSFET is based on the principle that an analyte in contact with a catalytic metal can produce a reaction at the metal surface. The limitation of MOSFET is that the reaction products must penetrate the metal layer in order to change the electrical properties of the device. SAW resonators are highly sensitive to both mass and acoustic impedance changes of the coatings in array elements. However, the micromanufacturing of large numbers of SAW elements into an integrated system is an extremely difficult task. In addition, the signal transduction mechanism requires complicated electronics. Similar limitations are found in arrays using TSM acoustic wave sensors. Optical sensor arrays require the use of complex instrumentation control systems, which increase fabrication costs and size. Also, optical sensors suffer from a restricted availability of light sources and a limited lifetime due to photobleaching.

Electrically conducting polymers are of interest for use as sensing elements in this technology. Electrically conducting polymers are a class of organic materials that exhibit conductivities approaching those of many metals. The chemical and electrical properties of electrically conducting polymers can be designed and controlled within several orders of magnitude by adjusting the pre-polymer formulation, e.g., the molar ratio of monomer/dopant, addition of a copolymer (i.e., organic polymer), additives, or the modification of the functional groups of the polymer backbone. Thus, the surface of an electrically conducting polymer film can be "tailored". The presence of structural features (e.g., aliphatic side chains, conjugation, heteroatomic functional groups, double bonds, and hydrogen bonds) in the polymer influences the response of the film to a given analyte. Since a different composition is used for each sensor element, an array of elements responds to a wide variety of chemicals in an identifiable mode. Thus, conducting polymers are well suited for an array sensor because the exposure to an analyte will induce a distinct pattern of responses.

Most of the sensing elements using electrically conducting polymers have been fabricated using a chemical or electrochemical procedure. In the electrochemical process, the polymer is grown on two closely spaced electrodes held at the same potential until a bridge of polymer is formed across these electrodes. This procedure allows the control of the oxidation state of the polymer. However, the transverse section cannot be controlled. Thus, a problem of repeatability exists in the electrochemical preparation of conducting polymers. To overcome this problem, very thick films of polymers have to be deposited. Despite high repeatability, responses of these films tend to be sluggish. Further, every element needs to be synthesized independently. Thus, the overall process of making conducting polymer sensors using electrochemistry is time consuming and expensive, and therefore, this process does not allow for mass production of microelectronic devices. Also, tailoring each sensing element by combining conducting polymers with organic molecules and/or polymers (OPs) (i.e., incorporation of OPs into the conducting polymer) is problematic due to technical limitations. For example, most OPs are insoluble in water, and not ionically charged, which substantially reduces the number of OPs that are compatible with the conducting polymer. Other drawbacks of conventional conducting polymers as sensor elements are: (i) they are susceptible to humidity; and (ii) they require extended cycle time (i.e., in the minute range) for sequentially processing samples.

Therefore, there is a long-felt need in the art for an array-based sensor device that overcomes limitations such as those of reproducibility, humidity susceptibility, high power consumption requirements, the need for wide selectivity and high sensitivity and the potential for mass production. There is a need as well for methods of preparing and using such sensors.

SUMMARY OF THE INVENTION

The present invention provides an array-based chemical sensor for detecting the presence of analytes in either a gas or liquid samples. This sensor comprises a plurality of electrode pairs; and a photopolymerized electrically conducting polymer composition in contact between each electrode pair, wherein each polymer composition may include a different organic polymer capable of interaction with different analytes. The sensor comprises a means for delivering a sample containing an analyte (or several analytes) to an exposed surface of each polymer composition and a plurality of electronic signal means for electronically signaling a change in a chemical and/or electronic property of each polymer composition due to the presence of the analyte. In a preferred embodiment, the sensor further comprises a nonconductive sensor chip substrate upon which the electrode pairs are disposed. In the most preferred embodiments, the substrate is either an alumina chip or a printed circuit board (PCB) (epoxy laminate).

Analytes may be organic molecules, such as volatile and semi-volatile organic carbons, or pollution by-products such as $NO_x$, or other toxic industrial materials. Different groups of analytes may be distinguished, such as alcohols, ketones, chlorinated organics, aromatics, organometallics, and inorganics. Differentiation between different analytes within a group can be achieved with a conductive polymer array sensor. For example, it is possible to differentiate benzene from toluene, trichloroethylene from chloroform, and methanol from ethanol.

The present invention further provides a process for detecting the presence of an analyte comprising the steps of concentrating vapors of a given analyte; exposing a sensor chip to the concentrated vapors; and measuring a signal indicating or representing resistance changes of electrically conducting polymers when exposed to the concentrated vapors by a means for signal processing.

The present invention further provides a process for making an array-based chemical sensor comprising the steps of distilling monomers capable of forming conducting polymers; formulating a monomer solution by mixing the distilled monomer with a first solvent containing an electron acceptor; adding a dopant to a first monomer solution; dissolving an organic polymer in a second solvent such as acetonitrile or tetrahydrofuran; blending the monomer solution and the organic polymer removing any immiscible residue from the blended solution; photopolymerizing the blended solution to form a polymer; and preparing sensing elements using composites of the polymer. The sensing elements may be prepared as three-dimensional sensing elements or two-dimensional sensing elements. In a preferred embodiment, the conducting polymer is selected from the group consisting of polypyrrole, polyaniline, thiophene, methylopyrrole and derivatives and mixtures thereof, and the organic polymer is selected from poly(caprolactone), poly(styrene/maleic anhydride) poly(4- vinylphenol), poly(vinylidene fluoride), and poly(N-vinylpyrrolidone).

The present invention will have wide application in the environmental industry (e.g., to gauge the effectiveness of environmental remediation efforts, to effect waste minimization, and to detect the presence of toxic, hazardous, or regulated chemicals in waste effluents, drinking water, and other environmental systems); in the food, beverage, and perfume industries, (e.g., for the determination of odors, flavors and aromas); in the agronomic industries (e.g., for sensing pesticides in water and in fresh produce, assessing livestock waste, and monitoring airborne pollen levels); in the clinical industry (e.g., as a breath diagnostic tool for disease screening and monitoring, to measure the degree of alcohol (ethanol) or 'hangover' extent (methanol) in breath, to provide a valuable measure of body burden and its relationship to inhalation exposure to VOCs); in the detection of chemical vapors associated with weapons of mass destruction, as well as in many other areas such as in the Gas and Chemical Industry and in Regulatory Agencies.

BRIEF DESCRIPTION OF THE DRAWINGS

So that the above recited features and advantages of the present invention can be understood in detail, a more particular description of the invention, briefly summarized above, may be had by reference to the embodiments thereof, which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
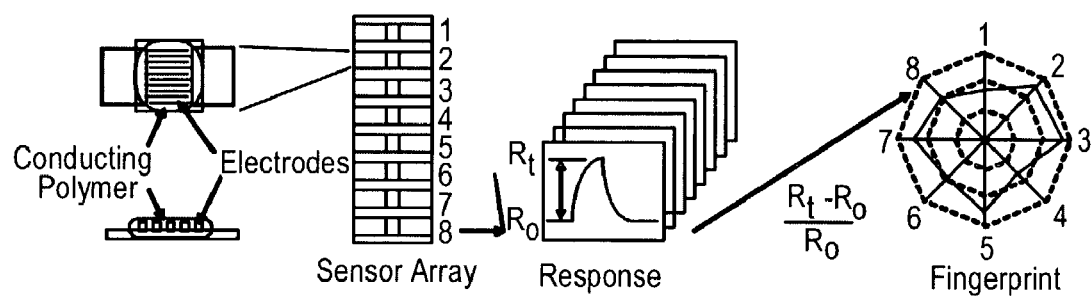
FIG. 1 is a schematic process flow diagram.

The present invention provides a novel array-based chemical sensor for detecting the presence of analytes in gas or liquid samples. The sensor comprises a plurality of contacts or electrode pairs, such as an eight-member interdigitated electrode structure. The sensor further comprises a plurality of photopolymerized electrically conducting polymer compositions in contact between each of the electrode pairs. Each polymer composition may include an organic polymer capable of interacting with one or more analytes. In a preferred embodiment, there is a nonconductive substrate such as an alumina chip, upon which the electrodes and the polymer compositions of the invention are disposed or deposited, for example by adhesion means such as gluing, soldering or other means of bonding. Typically, adhesion of the electrode pairs to the substrate is achieved by vapor deposition and adhesion of the conducting polymer to the substrate is achieved by photopolymerization.

The sensor also comprises a means for delivering samples to the polymer array, such as a vapor delivery system that blows the analytes over the array elements. A means for processing the resultant electronic signal from each polymer composition is provided in electronic communication with each electrode pair. The collective information from the signals provides a fingerprint that is unique to a particular analyte. The entire array will typically be contained within a sensor chamber.

Analytes of interest may be, but are not limited to, organic molecules, such as volatile and semi-volatile organic carbons (VOCs and SVOCs), organic and inorganic by-products of industrial pollution or toxic industrial materials (TIMs), such as HCl, $NO_x$, trichloroethylene (TCE), toluene and benzene, chemicals associated with weapons of mass destruction, odors associated to food freshness, drinks and perfumes, etc. Water vapor is also detectable by the sensor.

The present invention further provides a process for detecting the presence of analytes using the array-based chemical sensor. This process allows for the identification of an analyte of interest. The process of the present invention is capable of differentiating one group of chemicals from others on the basis of their physical or chemical characteristics and/or properties, such as hydrophilicity and polarity. Each sensor element is capable of generating an output signal into a software-based pattern recognition algorithm for analyte identification. While a pattern recognition algorithm may be created in any manner, the pattern recognition algorithm may created using an artificial neural network programmed with MatLab® Neural Network Toolbox (available from The Mathworks, Inc. of Natick, Mass.). The algorithm developed in MatLab® can be exported as C code, which can easily be incorporated into a microcontroller program, that can be part of the sensor ancillaries. Optionally, other Chemometrix methods are commercially available (e.g., Eigenvector, Mason, Wash.). The output signal is a result of electrical resistance changes in the electronically conducting polymers when exposed to a given analyte.

FIG. 1 is a schematic process flow diagram that summarizes several aspects of the sensor construction and operation. A conducting polymer composition is deposited between a pair of electrodes, most preferably interdigitated electrodes. A plurality of these electrodes and conducting polymer compositions may be used in combination to form a sensor array, shown here including a set of eight individual sensor elements although any number of sensor elements can also be used. Upon passing an analyte over the array, one or more of the sensor elements experiences a change in electronic resistance that can be measured. The collection of measured changes, in the form of response signals, may be referred to as a "fingerprint" that is unique to a particular analyte and may be used to qualitatively identify the analyte, quantitatively measure the amount or concentrations of the analyte, or both.

A preconcentrator is preferably used in order to lower the detection limit of the analyte vapors. Preconcentrating the vapors enables detection of some vapors that would not be detectable without a concentration aid. The preconcentrator preferably uses the "purge and trap" method, such as that used in gas chromatographic (GC) analysis.

The present invention further provides a process for making an array-based chemical sensor. This process mixes organic polymers with conducting polymers. The use of conducting polymers provides conductive properties to each of the sensing elements in the array, and the inclusion of organic polymers provides specific chemical or functional groups that interact with the analytes. In a preferred embodiment, the conducting polymers are prepared by a photopolymerization procedure.

Preferably, the monomers used to prepare the conducting polymers, such as pyrrole, methyl pyrrole, thiophene and aniline, are distilled before each preparation of the conducting polymers. In order to then formulate the conducting polymers, the distilled monomer mixture is then mixed with a solvent containing an electron acceptor or dopand. Examples of dopands include p-toluenesulfonic acid monohydrate (pTSA), 1-octanesulfonic acid sodium salt (OSA), camphorsulfonic acid (CSA), anthraquinone-2-sulfonic acid sodium salt (ASA), lithium perchlorate (PER), 4-octylbenzenesulfonic acid sodium salt (OBS), and 3-nitrobenzenesulfonic acid sodium salt (NBS). A critical issue is the solubility of the dopant in the pre-polymer formulation. This required dissolution in acetonitrile. However, none of these dopants dissolved in acetonitrile. An alternative method consists of mixing the dopant dissolved in deionized water with the pre-polymer formulation. Out of 8 dopants, CSA and pTSA are successfully mixed with the pre-polymer formulation and provided reliable sensor elements. In a preferred embodiment of the invention the solvent is acetonitrile and the electron acceptor is $AgNO_3$. A mixture of two or more conducting polymers such as pyrrole and methylpyrrole, pyrrole and aniline, or pyrrole and thiophene, may also be used.

The organic polymers, which are to be mixed with the conducting polymers, are subjected to a solubility test. In a preferred embodiment, 0.1 g of an organic polymer is dissolved in 1 mL of either acetonitrile or tetrahydrofuran. The organic polymers are preferably selected from poly acetal resin, polyacrylamide, polyacrylic acid, polyacrylonitrile/butadiene/styrene, polybutanediol terephthalate, poly-n-butyl methacrylate, poly-iso-butyl methacrylate, poly-n-butyl methacrylate/iso-butyl methacrylate, poly caprolactam, poly caprolactone, polycarbonate bisphenol A, polyethylene, polyethylene/acrylic acid, polyethylene/maleic anhydride, polyethylene oxide, polyethylene vinyl acetate, polyethylmethacrylate, polyhexamethylene adipamide, polyhexamethylene dodecanediamide, polyhexamethylene sebacamide, polylaurolactam, polymethylmethacrylate, poly-alpha-methylstyrene, polypropylene, chlorinated polypropylene, polystyrene, polystyrene allyl alcohol, polystyrene/maleic anhydride, polysulfone, polytetrafluoroethylene, poly vinyl acetate, poly vinyl alcohol, poly vinyl butyral, poly vinyl chloride, poly-4-vinylphenol, polyvinylidene chloride/acrylonitrile, polyvinylidene chloride/vinyl chloride, polyvinylidene fluoride, poly vinyl methyl ether/maleic anhydride, poly N-vinylpyrrolidone and mixtures thereof. Acetonitrile is used because it can dissolve the structural material of the conducting polymers, as well as the electron acceptor. Tetrahydrofuran is used because it can dissolve most of the organic polymers listed above.

The conducting polymers and the organic polymers are then mixed together, preferably in a volume ratio of between 1:10 and 10:1. Changing the volume ratio allows changing the initial resistance of the conducting polymer, and also to some extent, some of its properties. The blended formulation is then vigorously shaken and vortexed. Any unmixed portion is discarded at this point. After the formulations have been prepared, the process of the present invention provides for photopolymerization of the polymer composite. The unique photopolymerization process of U.S. Pat. No. 6,210,537, incorporated herein by reference, does not require a conductive substrate to deposit polymer films. This renders the process compatible with standard practices of the electronic board technology, allowing for optimal fabrication of the sensor array on a printer microcircuit board with standard electronic controls. The method uses UV light as the driving force to induce the polymerization process. The photo-polymerization process allows each sensing element to be uniquely formulated by adding diverse organic compounds to each formulation. The presence of structural features (such as aliphatic side chains, conjugation, heteroatomic functional groups, double bonds, and hydrogen bonds) in the polymer influences the response of the film to a given analyte. Since a different composition is used for each sensing element, an array of elements can respond to a wide variety of chemicals in an identifiable fashion. The chemical and electrical properties of these compositions can be designed and controlled within several orders of magnitude by adjusting the molar ratio of monomer/dopant, addition of a copolymer, or the modification of the functional groups of the polymer backbone. In a preferred embodiment, a preliminary test is carried out to evaluate the resistance properties of the conducting polymer. For this, 1 $\mu$l of a successful blending of the conductive polymer and the organic polymer is used to draw a line on an epoxy/glass composite laminate. This is followed by UV illumination over a period of about 10 minutes to achieve photopolymerization.

The photopolymerized conducting polymer composite is allowed to air dry before the resistance of the polymer line is measured with an ohmmeter. Resistance values are preferably between 1 $\Omega \cdot cm$ to 100 $M\Omega \cdot cm$, most preferably between 10 $k\Omega \cdot cm$ and 10 $M\Omega \cdot cm$. The conducting polymer to organic polymer ratio in the formulation may be varied to achieve a desired electrical resistance. Once the formulation has been prepared to produce resistance values in the desired range, the formulation is applied to the interdigitated electrodes and photopolymerized to produce the composite sensing elements. In a preferred embodiment, 0.2 $\mu L$ of a successful blending of the conducting polymer and organic polymer is deposited on top of an interdigitated electrode. This is followed by 10 minutes of UV illumination to achieve photopolymerization.

Finally, the process of the present invention provides for the preparation of both 2-dimensional and 3-dimensional sensing elements.

EXAMPLES

Photopolymerization of New Conducting Polymers

Most conducting polymers prepared electrochemically using pyrrole, methylpyrrole, thiophene, phenylene, 5-carboxyindole, etc., are of limited use because of the complexity of the preparation processes. An alternative process, photopolymerization, using pyrrole or pyrrole/aniline mixtures has been successfully developed. The foremost advantage of the photopolymerization process is that the conducting polymers are formed on any substrate—conductive or nonconductive. The photopolymerization process was tested on other monomers such as aniline, methylpyrrole, and thiophene.

Aniline

Four different amounts (0.15, 0.3, 0.6, and 1.2 mL) of distilled aniline were mixed with 0.3 mL acetonitrile dissolving 0.3 g of $AgNO_3$. 1 $\mu L$ of the mixture was use to draw a line on epoxy laminates and was illuminated by the UV light for 10 minutes. Resistance values of the conducting polymer lines were measured with an ohmmeter. As the volume of aniline in the formulation increased (i.e., the concentration of $AgNO_3$ in the mixture decreased), the resistance values increased. From this experiment, it was found that it was possible to polymerize polyaniline via the photopolymerization technique, and that the resistance of the conducting polymer was dependent on the concentration of photopolymerization initiator, $AgNO_3$.

Thiophene

The same procedure was carried out for the photopolymerization of polythiophene. The resistance values depended on the fraction of thiophene in the formulation, as in the case of polyaniline. As the volume of thiophene in the formulation (including 0.3 mL acetonitrile dissolving 0.3 g $AgNO_3$) increased from 0.15 to 0.6 mL, the resistance of the polythiophene lines on the epoxy laminates also increased. The photopolymerized polythiophene had about ten times lower resistance values than the photopolymerized polyaniline.

Photopolymerization of Blend of Conducting Polymers and Organic Polymers

The basic formulation to prepare a polypyrrole conducting polymer consists of: (i) mixing 0.075 g $AgNO_3$, 1 mL acetonitrile (AcCN), and 0.5 mL distilled pyrrole (the "prepolymer formulation"), and (ii) exposing an aliquot of the formulation under UV light for 10 minutes. Optionally, dopants and organic polymers (OPs) are added to the prepolymer formulation to provide diversity to the sensor elements. Polypyrrole is responsible for the conduction in the conducting polymer. Dopands modify the electrical properties of pyrrole. Dopants and OPs, as well as polypyrrole, are responsible for interactions with analytes. Polypyrrole (the basic component of the photopolymerized conducting polymer) shows to be itself a sensor element responding to some VOCs and TIMs.

Out of 44 organic polymers tested, seven could be dissolved in acetonitrile. These organic polymers were: polycaprolactone, polyethylmethacrylate, polymethylmethacrylate, polystyrene/maleic anhydride, polyvinylacetate, polyvinylphenol, and polyvinylpyrrolidone. Formulation of blends was 1 mL pyrrole, 1 g $AgNO_3$, 1 mL acetonitrile, and 0.03 g of organic polymers. Photopolymerization was successful for all of the seven organic polymers (Table I) when pyrrole was used.

These results clearly show that the photopolymerization process is a flexible procedure that can produce a series of electrically conducting polymer compositions with different functionalities, depending on the pre-polymer formulation. Also, these results indicate that polymer-based sensors can have a wider combination of sensor functionality than metal oxide-based sensors.

TABLE I

Blends of conducting polymer and organic polymer dissolved in THF.[1]

| Organic Polymer | Photopolymerization[2] | Resistance ($k\Omega \cdot cm$) |
|---|---|---|
| Poly(acrylonitrile/butadiene/styrene) | 4 X, 10 minutes | 28 |
|  | 3 X, 10 minutes | 4.4 |
| Poly(ethylene/maleic anhydride) | 4 X, 10 minutes | 12 |
|  | 3 X, 10 minutes | 17 |
| Poly(ethyl methacrylate) | 4 X, 10 minutes | 30 |

TABLE I-continued

Blends of conducting polymer and organic polymer dissolved in THF.[1]

| Organic Polymer | Photopolymerization[2] | Resistance (kΩ · cm) |
|---|---|---|
| | 3 X, 10 minutes | 34 |
| Poly(styrene/acrylonitrile) 75:25 | 4 X, 10 minutes | 25 |
| | 3 X, 10 minutes | 28 |
| Poly(styrene/allyl alcohol) | 4 X, 10 minutes | 17 |
| | 3 X, 10 minutes | 5.1 |
| Poly(styrene/maleic anhydride) 50:50 | 5 X, 10 minutes | 30 |
| | 3 X, 10 minutes | 24 |
| Poly(vinylidene chloride/acrylonitrile) | 4 X, 10 minutes | 37 |
| | 3 X, 10 minutes | 4.3 |
| Poly(vinylidene fluoride) | 4 X, 20 minutes | 39 |
| | 5 X, 10 minutes | 32 |

[1]Basic formulation for the photopolymerization process was 0.2 mL of conducting polymer (CP) formulation (1 g AgNO$_3$, 1 mL acetonitrile, and 1 mL pyrrole) mixed with 0.2 mL of OP formulation (0.1 g organic polymer dissolved in 1 or 3 mL THF).
[2]Number in front of X indicates the number of "coatings" (i.e., number of photopolymer films) used to prepare a given sensor element Table II shows an example of a sensor array prepared with eight different photoconducting polymer formulations.

TABLE II

Composition of an array sensor utilizing photopolymerized conducting polymer formulation.

| Channel | Formulation |
|---|---|
| #0 | 0.1 mL of 10% CSA in DI water + 1.5 mL pre-polymer formulation (CP/CSA) |
| #1 | 0.075 g AgNO$_3$, 1 mL acetonitrile, 0.5 mL pyrrole (conducting polymer, CP) |
| #2 | 5% poly(ethyl methacrylate) in THF, blended in 0.1:1.0 ratio with pre-polymer formulation (CP#18) |
| #3 | 5% poly(iso-butyl methacrylate) in THF, blended in 0.2:1.0 ratio with pre-polymer formulation (CP#8) |
| #4 | 0.1 mL of 10% pTSA in DI water + 1.5 mL pre-polymer formulation (CP/pTSA) |
| #5 | 5% Poly(styrene/maleic anhydride) 50:50 in THF, blended in 0.1:1.0 ratio with pre-polymer formulation (CP#30) |
| #6 | 5% Poly(methyl methacrylate)in THF, blended in 0.1:1.0 ratio with pre-polymer formulation (CP#23) |
| #7 | 5% Poly(vinyl butyral) in THF, blended in 0.1:1.0 ratio with pre-polymer formulation (CP#36) |

Dispensing System

The sensor polymer material had to be deposited in a controlled fashion onto the interdigitated electrode areas of the substrate chip. In one approach, it is done using a micro pipette. However, the reproducibility of the sensors is not satisfactory. In a preferred embodiment, a mechanical dispensing system is used to accomplish a precise deposition of the sensor material. The system consists of an X,Y,Z-table (Enco® Tools) and a 10 μL GC injection syringe (Hamilton®) mounted to the table. A 50-point manual step dispenser (Cole-Parmer®) feeds the syringe plunger for a precise metering of 0.2 μL volume. The procedure for the sensor deposition is as follows: the components of the polymer solution are prepared inside a 4 mL vial. The content is well mixed and quickly placed under the syringe. The plunger is operated 3 times up and down to ensure a good mixture in the syringe and its needle (26 s gauge with flat bottom). Then the chip substrate is moved into position on the 3-axis table. With the tip of the needle approximately 0.01" above the substrate, the 50-point feeder is pressed once to apply 0.2 μL sensor material onto the chip. The needle is then lifted up quickly to allow the small drop of solution to form a smooth meniscus and air dried. The syringe is then rinsed with acetonitile for the next formulation.

Figure 2:
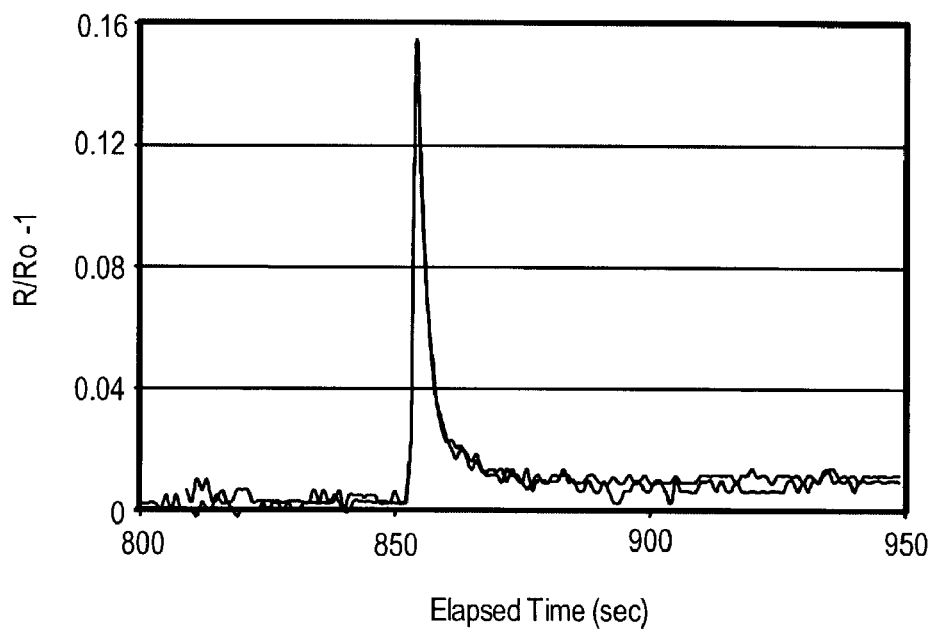
FIG. 2 is a graph showing the signals from two sensor elements fabricated from the same conducting polymer formulation when exposed to a pre-concentrated sample from 1 ppm TCE aqueous solution.

FIG. 2 provides an example of the reproducibility achieved by this approach. There, the signals from two different sensor elements fabricated from the same polymer formulation are shown when exposed to a pre-concentrated sample from 70 mL 1 ppm TCE aqueous solution. The signals are identical.

To further reduce fabrication tolerances, a fully automated and computer-controlled mixing, positioning, and dispensing system can be used. It is based on a robotic three-axis gantry positioner, e.g., "MiniRobo III", manufactured by Super Tech & Assoc. Phoenix, Ariz. The prepared sensor material is provided in a 4 mL vial. First an ultrasonicating wand (e.g., Vibra Cell VC130PB, Sonics & Materials, Inc., Newtown, Conn.) is inserted into the vial and sonicates the mixture for 5 seconds at a power level of 5 Watts. This mixing protocol produces good results without damaging the long-chained polymer molecules. When the wand is removed, the robotic gantry positioner inserts the syringe needle into the vial, and draws up a 10 μL sensor formulation. The needle is then precisely positioned over the chip substrate and 0.2 μL sensor formulation is dispensed on top of the interdigitated electrode (IDE) structure. In a preferred embodiment, the needle has a flat tip, which is close enough to the IDE surface such that the dispensed droplet touches the chip. This is necessary, because a 0.2 μL droplet is far too small to drip by itself from the needle tip. After deposition, the needle is moved up to allow the mixture to form a homogeneous bead. The syringe is moved over a waste bin and the remaining mixture is ejected. Then, it is inserted into a vial of cleaning solution, draws up the agent, ejects the contents over the waste bin, and repeats this procedure several times. Then the system is ready for the next sensor mixture.

Sensor Chamber

Figure 3A:
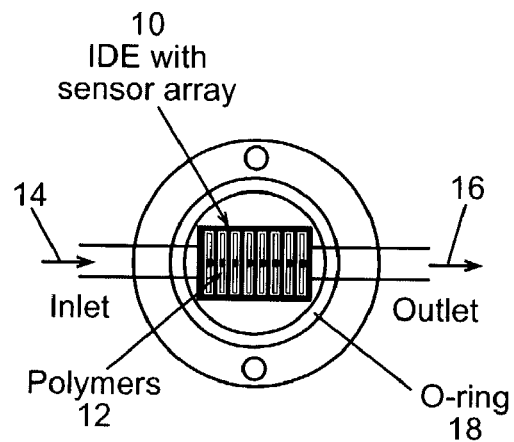
FIGS. 3A, 3B and 3C are schematic top, side and plan views of a sensor chamber.
Figure 3B:
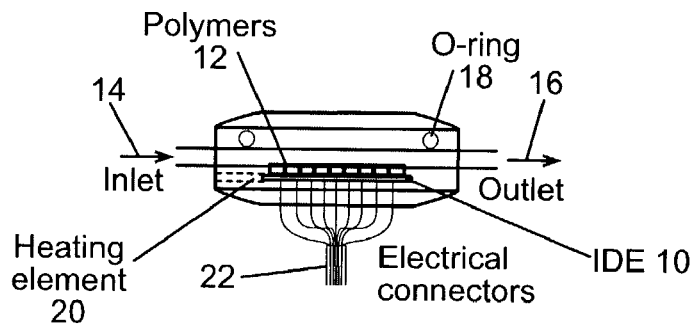
Figure 3C:
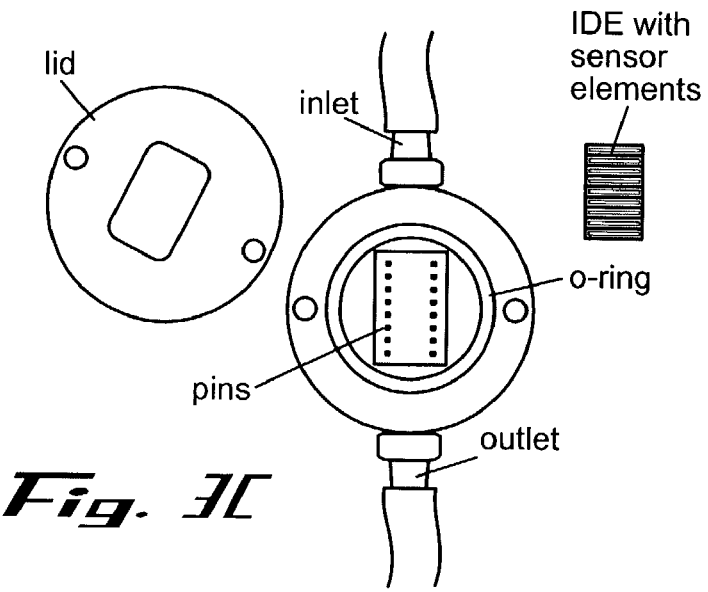

FIGS. 3A, 3B and 3C are schematic top, side and plan views of a sensor chamber containing a sensor array 10 having individual polymer sensor elements 12. The sensor chamber has an inlet 14 and an outlet 16, and the chamber is preferably made of a material with minimum absorption of organic and inorganic vapors, such as titanium. The chamber is preferably also made leak-proof, such as by the use of an o-ring 18 between a main chamber body 28 and a lid 26. Electrical connectors 22 may be attached to the chip through the use of pushpins 24 fixed inside the chamber. In one embodiment, the sensor array 10 is connected to the data acquisition board through a 20-pin IDE connector. It is preferred to also have a thermocouple and a cartridge heater 20 inserted in the chamber for temperature control. The sensor chamber is preferably made with a small dead volume to facilitate the contact between the analyte in the gas and the sensor element surface. While the dead volume of the chamber available to receive an analyte-containing fluid may be any suitable volume, the volume is preferably less than 10 mL, more preferably less than 5 mL, and most preferably less than 0.5 mL.

Analyte Delivery System

Figure 4:
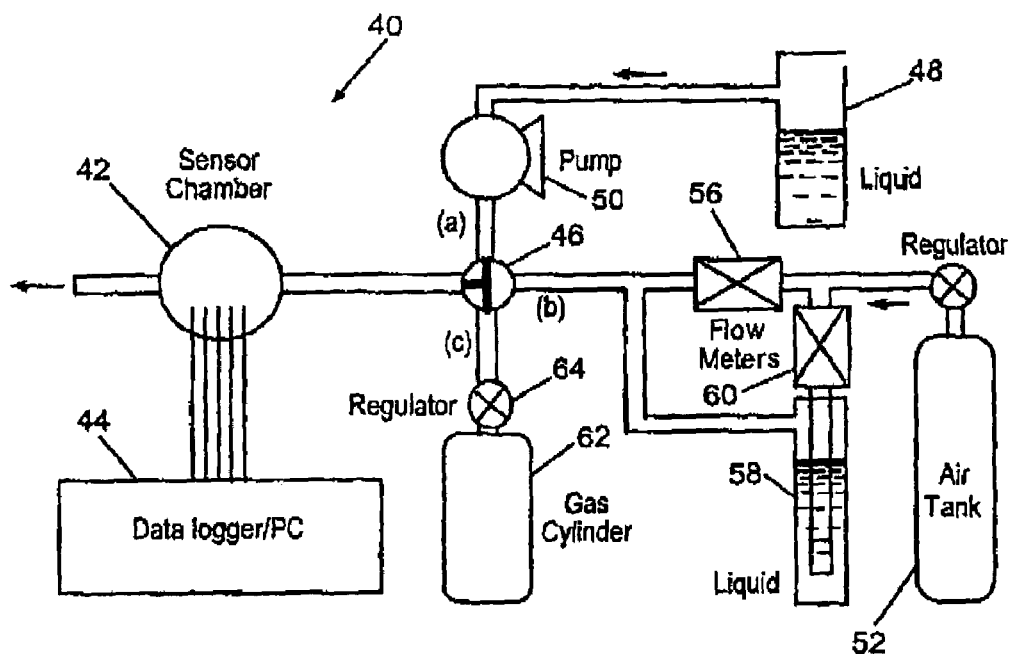
FIG. 4 is a process flow diagram of an analyte delivery system.

FIG. 4 is a process flow diagram of an analyte delivery system 40. Analytes in the gas phase (e.g., vapors representing TIMs, VOCs, and chemical warfare surrogates) are introduced into the sensor chamber 42 using one of three different approaches for vapor generation: (i) dynamic headspace; (ii) flow injection; and (iii) standardized compressed gas cylinder. In the dynamic headspace approach represented by route (a) in FIG. 4, a pump 50 takes analyte vapor (over a container 48 of the analyte, such as a concentrated HCl solution) into the sensor chamber 42. In the flow injection approach represented by route (b) in FIG. 4, a vapor is generated by purging air (or an inert gas like He) from a compressed gas cylinder 52 with a regulator 54 to a vessel 58 and out through a diffuser inside a liquid containing the analyte. A flowmeter 56 controls the rate of air flow directly to the chamber 42 and a flowmeter 60 controls the rate of air flow into the vessel 58. In the third approach represented by route (c) in FIG. 4, a standardized compressed gas cylinder 62 containing the analyte of interest (e.g., Matheson® Gas Products) and including a regulator 64 is used. A three-way valve 46 is shown, allowing selection of the gas source between route (a) to generate a quick qualitative response, route (b) for quantitative analysis, and route (c) to test the system response when a dilute sample is used. The flow rate of the analyte-containing gas through the sensor chamber can vary. In a preferred embodiment, a flow rate of 20 mL/min is used. In any of the processes described here, the analyte in the gas phase can be further diluted by mixing it with another gas, such as air. In addition, humidity can be introduced into the gas sample by bubbling air (or an inert gas) through water at a given temperature, and then mixing it with the gas containing the analyte vapor. Mixing of gases containing different analytes is also possible.

The concentration of organic chemicals in any route may be determined by means of a gas chromatograph or other suitable instrument.

For analytes present in water, ambient air may be bubbled into the water sample using a sparger preferably at a flow rate of 150 mL/min. The generated vapor is then fed into either the chamber or the preconcentrator.

Signal Processing

Figure 5:
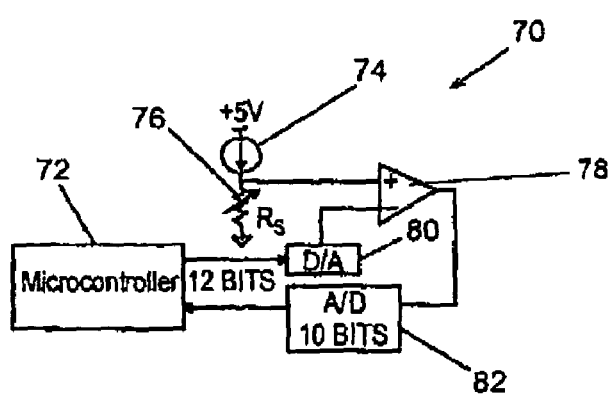
FIG. 5 is a schematic diagram of a module used to measure small resistance variations of the sensor elements.

FIG. 5 is a schematic diagram of a module 70 used to measure small resistance variations of the individual sensor elements 76 on a circuit board having eight channels to process the incoming signals from the sensor array. The objective is to measure small variations, such as 0.25 Ω, of a given sensor resistance when the initial resistance is large, such as 1 MΩ. To achieve this in all the channels, a "dynamic bridge" structure is used. There, a Digital to Analog (D/A) converter 80 and a microcontroller 72 form one branch of the bridge while a constant current source 74 and the sensor itself (76) form the other branch.

The sensor 76 having an electrical resistance (Rs) is provided in electronic communication with a voltage source 74, such as a power supply or regulator, preferably providing a potential of about +5V. The microcontroller 72 of FIG. 5 provides an output signal representing the sensor resistance as the resistance of the polymer composition changes as a function of time, that can be provided to a computer, such as the data logger/PC of FIG. 4, for data analysis.

A loop is closed with the D/A converter 80, the amplifier 78, the A/D converter 82, and the microcontroller 72. The system is always trying to make the error signal between the two inputs of the instrumentation amplifier equal to zero, thus keeping the "bridge" balanced. First, the program inside the microcontroller sends a value of hexadecimal 800 to the D/A converter 80. With a D/A voltage reference of +5 Volts, it outputs +2.5 Volts to the negative input of the instrumentation amplifier. This voltage is compared to the voltage drop across the sensor 76 and the difference is amplified 2000 times before being fed to the A/D converter 82 in the microcontroller 72. The microcontroller 72 reads this difference and decides whether to increase or decrease the signal to the D/A converter 80 in order to match the voltage signal coming from the sensor 76. Finally the microcontroller 72 sends both signals, the one being fed to the D/A converter 80 and the one being read from the A/D converter 82. The computer further processes and combines these two signals to deliver a result in the form of a resistance value.

In order to reduce noise in the output signal, measurements are preferably taken at a rate between 30 and 250 readings per second, then the arithmetic mean or average of the resistance measurements is calculated and the averaged data is sent to the computer every second for data acquisition. The system can measure variations as small as 0.25Ω in 1 MΩ signals. Similar systems can be fabricated to process incoming signals from bigger sensor arrays, e.g., 16, 24 or 32 elements, or any other desired number of elements.

Pre-Concentrator

One important factor to achieve high signal resolution is the use of a detection system with high sensitivity and low noise, such as the one described above. The use of a preconcentrator could also significantly enhance the signal resolution. A preferred preconcentrator is based on a "purge and trap" method, widely used in GC systems. All the required steps for the preconcentrator can be controlled by the use of a computer or a microprocessor. The heater control loops can be programmed to a preset absorption and desorption temperature for the preconcentrator. Both the preconcentrator heater and the chamber heater maintain the set temperature to within <1.5% with a PID control loop.

Figure 11A:
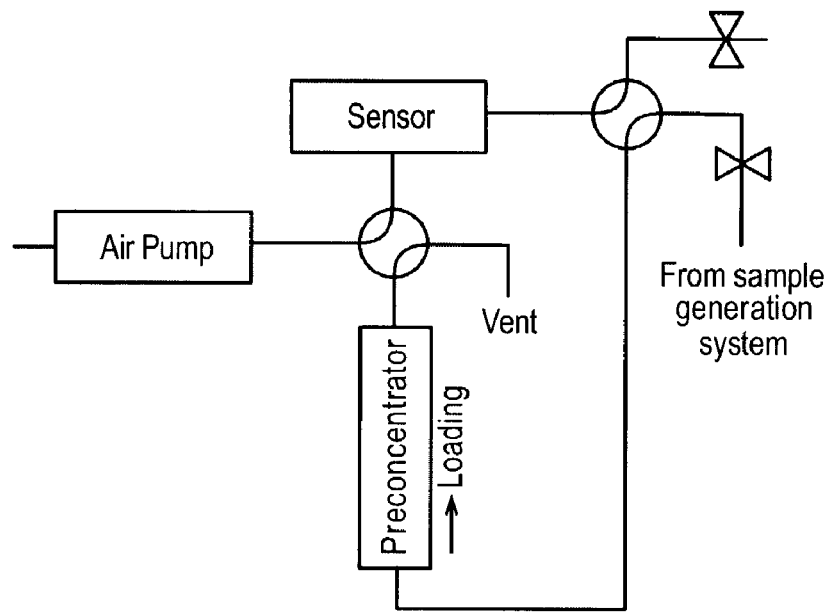
FIGS. 11A and 11B are schematic process diagrams illustrating the trap stage of the analyte and the desorption, monitoring, and release stage of the analyte, respectively, when a preconcentrator is used.
Figure 11B:
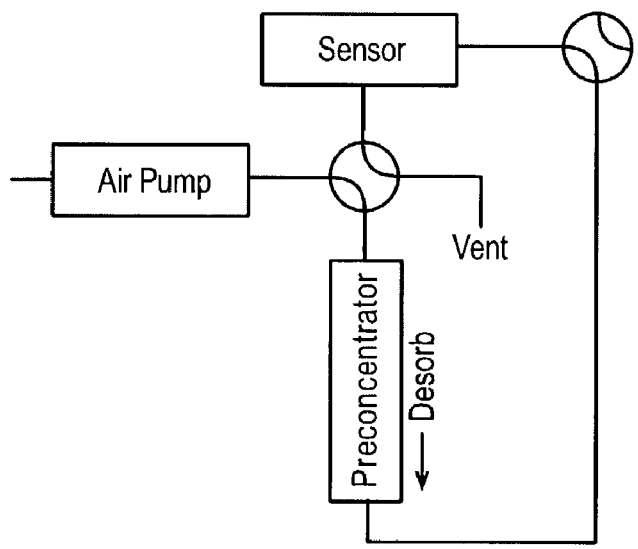

FIGS. 11A and 11B are schematic process diagrams illustrating the trap stage of the analyte and the desorption, monitoring, and release stage of the analyte, respectively. FIG. 11A shows the sample vapor from the sample generation system being directed into the preconcentrator, which traps the analyte. During this "trapping" stage, data is taken with the sensor, which is maintained at a constant temperature to minimize the response due to temperature changes. Data acquired during this stage are averaged to establish a baseline. The length of the "trapping" time (and number of points used in obtaining the baseline) can be adjusted by the user. When this time has been reached, the trap stage is complete, the airflow is stopped, and the next stage begins.

FIG. 11B shows the control valves repositioned to provide the correct flow for the monitor stage. The preconcentrator begins to be heated up to its release temperature. During heating, all airflow is stopped temporarily to prevent dispersion of the analytes as they are released from the preconcentrator. When the release temperature is reached, a miniature pump is turned on at a slow airflow rate (typically 20 mL/min). This air flows through the preconcentrator in the opposite direction from which it was loaded, releasing the concentrated plug of analytes. This plug is moved into the sensor chamber, where it contacts the sensor elements.

For application requiring miniaturization, the sampling valve is eliminated by employing a reversible mini-air pump (with dimensions 1.5" long and ¾" cylindrical diameter) serving both, the sample and purge mode. The pre-concentrator consists of a 2×2 mm small SiN membrane on a microchip instead of the conventional 4"×¼" glass tube. Thermal management is improved by orders of magnitude achieving 200° C. in 10 msec using only 100 mW of power.

Example 1

Construction of a 3-Dimensional Sensing Element

The photopolymerization process allows the fabrication of 3-dimensional elements. This has the advantage of providing a high surface area for interaction between the sensor element and the analyte. To prepare a 3-dimensional sensing element, the blended photopolymerized composite is applied to a cylindrical substrate, e.g., a fishing line. In a preferred embodiment, the line is 2" long and 0.024" in diameter. The line is then put on a slow speed rotor under UV light illumination for 10 minutes. In a preferred embodiment, a 200 W Hg-Xe ORIEL® lamp (Oriel Corporation, Stratford, Conn.) with a collimator is used. This process is repeated until the desired resistance is attained. Then the fishing line with the polymerized polymer composite is cut to a length of about 0.5" and each end of the line is crimped onto a metallic connector such as a female D-sub crimp pin. One of the metal connectors is wrapped with a heat-shrinkable tape to identify the conducting polymer and prepared sensing elements are then put into a sensor board.

Example 2

Construction of a 2-Dimensional Sensing Element

For many applications, a miniaturized sensor array is desirable. In such cases, an array sensor can be fabricated using 2-dimensional elements, deposited, for example, on interdigitated electrodes (IDE) on a printed circuit board (PCB) or alumina chip. An example of a substrate for the fabrication of an array of 2-dimensional elements consists of eight-member IDE structure on an alumina chip substrate of dimension of 2 cm×1 cm. Each IDE structure has an area of 1 mm×1 mm. The interdigitated electrodes as well as lead-out stripes are gold-coated, approximately 450 nm thick. The spacing between the electrodes in the IDE structure can be varied, with a most preferred embodiment of 25 $\mu$m spacing. Both edges of the IDE structure are connected to wider strips (4.5 mm×1 mm) at the edges of the alumina chip. An 0.2 $\mu$L aliquot of the polymer mixture was applied to the IDE structure and the chip was placed under UV illumination for 10 minutes. Following successful polymerization, metallic leads on the chip were soldered to a sensor board, which included a 20-pin socket. A schematic of the resulting device is shown in FIGS. 3A, 3B and 3C having an IDE with sensor array 10. Vapors to be sensed by the array are blown, such as by a fan or pump, in through the inlet 14 and exit the outlet 16. Sensing polymers 12 respond to the vapors and their responses are transmitted to a microcontroller or computer (not shown) by electrical connectors 22 that communicate with the polymers 12 through the pins 24. The device also includes a heating element 20 and an O-ring 18 that forms an gas tight seal between the main chamber body 28 and the lid 26. It should be recognized that the sensor chamber containing the polymers and receiving the vapors may having any shape or configuration and that the polymers and electrodes may be disposed within the chamber in any arrangement.

Example 3

Response of Individual Sensing Elements to TIM'S

Figure 6:
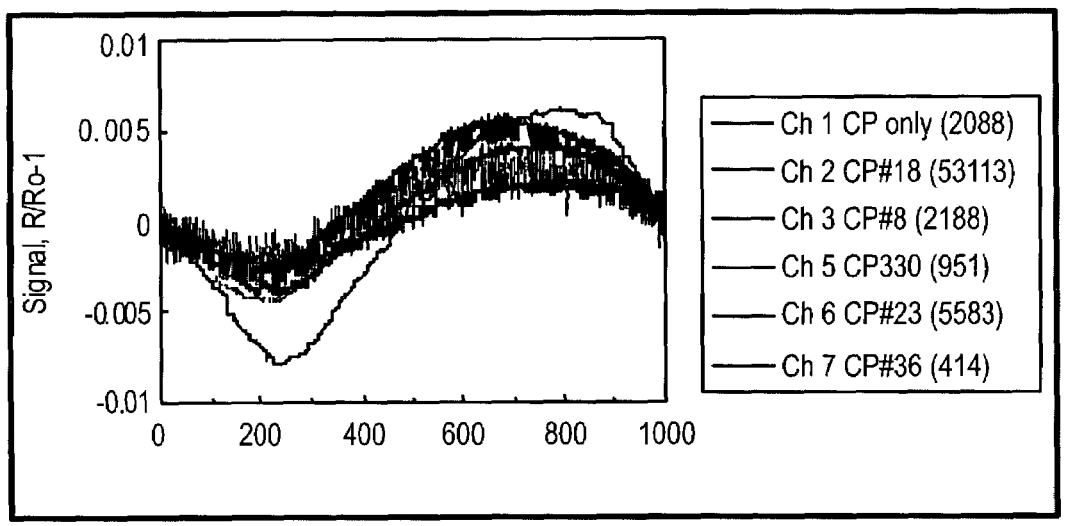
FIG. 6 is a graph of the response signals from an array of elements.

A sensor array (cf., Table II) containing 8 different conducting polymer elements was exposed to 50 ppm ammonia in He (OSHA Permissible Exposure Limit (PEL) for ammonia is 50 ppm determined by an 8-hour time weighted average (TWA)). Pure He was fed before and after the exposure to ammonia gas. FIG. 6 is a graph of the response signals from the array of different elements in Table II. The graph shows that an array of photopolymerized conducting polymers can be used for the detection of ammonia at the OSHA PEL TWA. The numbers in parenthesis are the resistance values (in ohms) measured at time 0.

Example 4

Response of Sensor Chips to TIMs, VOCs and Surrogate of Warfare Agents—"Fingerprints"

Figure 7A:
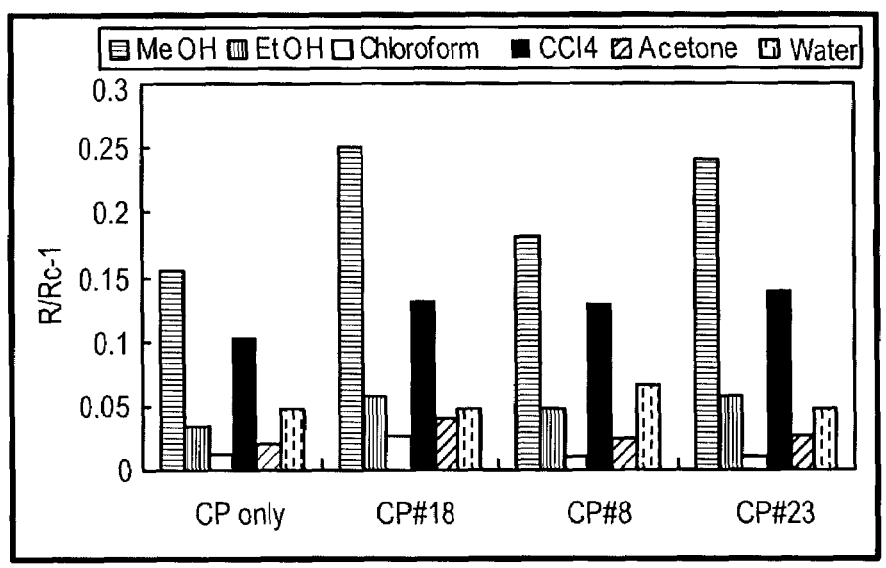
FIGS. 7A and 7B are bar charts showing the "fingerprints" of several chemical vapors.
Figure 7B:
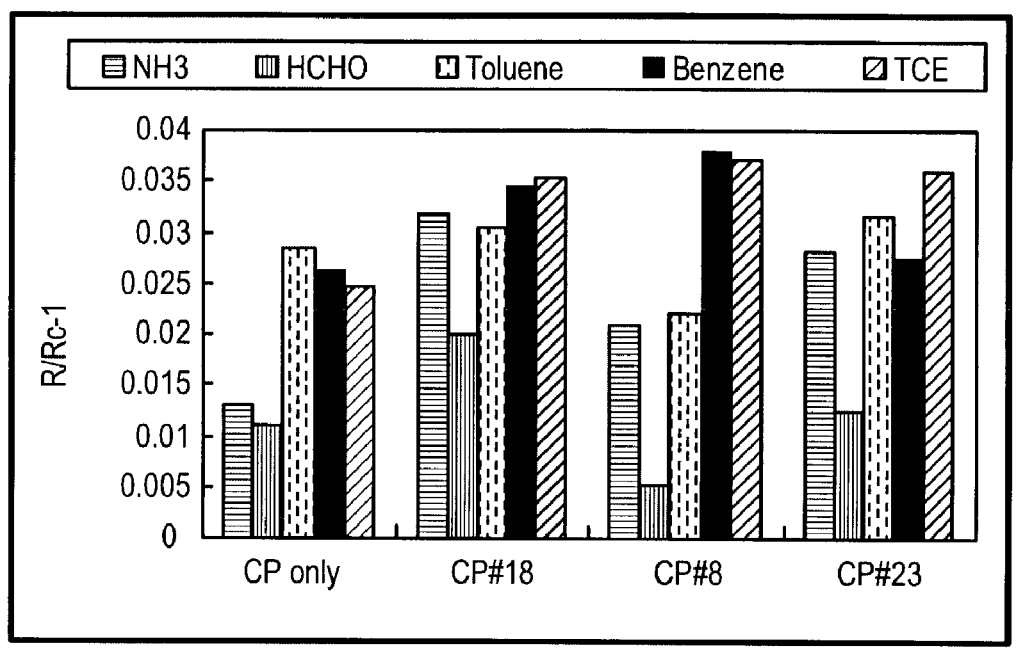

Chemical vapors including some TIMs and VOCs were tested using photopolymerized conducting polymers prepared as an array sensor. Ammonia vapor was fed into the sensor chamber using standardized gas cylinders. Other vapors (formaldehyde, methanol, water, ethanol, toluene, benzene, chloroform, tetrachloromethane, trichloroethylene, and acetone) were fed into the sensor chamber at flow injection analyser mode using ambient air as the carrier gas. Each solvent was purged for 2 min and the signals, $R/R_c-1$, at 2 min were registered as numerical signatures of the vapor. FIG. 7 provides a pair of bar charts showing the "fingerprints" for the chemical analyte vapors mentioned above. The corresponding polymer compositions are given in Table II. Although the response from only four sensors is shown here, a different "fingerprint" was produced for each chemical. More differentiation can be achieved by the incorporation of more sensor elements.

An important observation is that water was identified as another analyte, and it did not mask the signal from other analytes (i.e., response to water was at or below levels for most of the other analytes). This is an important result, because signal interference from water is a problem known for most array sensors using conducting polymers.

Figure 8:
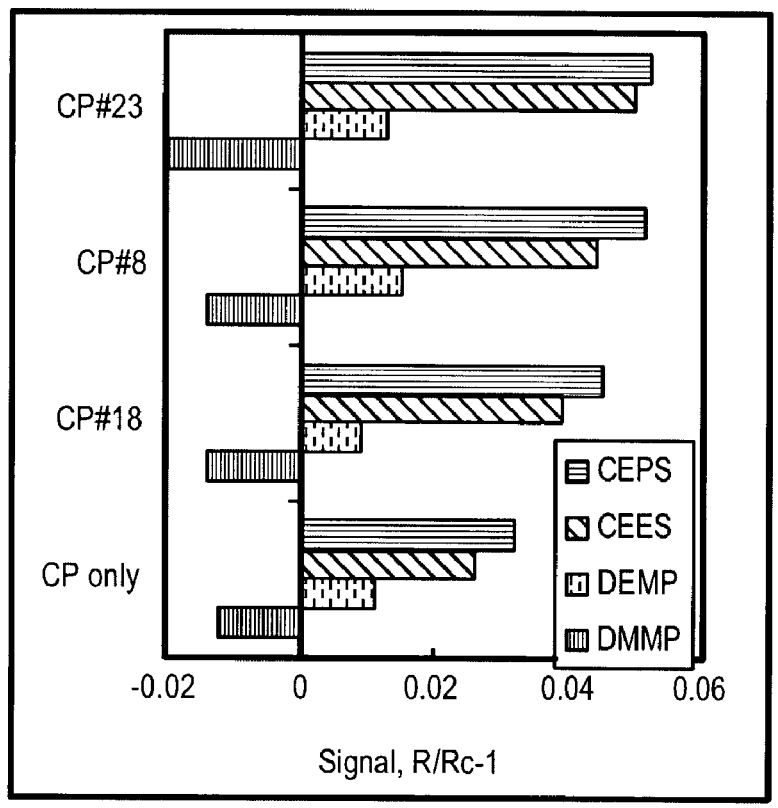
FIG. 8 is a bar chart showing the "fingerprints" of several chemical warfare surrogates.

Four chemical warfare agent surrogates were also tested on the sensor array. Dimethylmethyl-phosphonate (DMMP) and diethylmethylphosphonate (DEMP) are surrogates for Sarin (GB) and Soman (GD). Chloroethylethylsulfide (CEES) and chloroethyl-phenylsulfide (CEPS) are surrogates for Mustard gas (HD). Vapors of these surrogates were generated using the flow injection system. FIG. 8 is a bar chart showing the "fingerprints" of the chemical warfare surrogates mentioned above. The corresponding polymer compositions are given in Table II.

Example 5

Concentration Dependance

Figure 9:
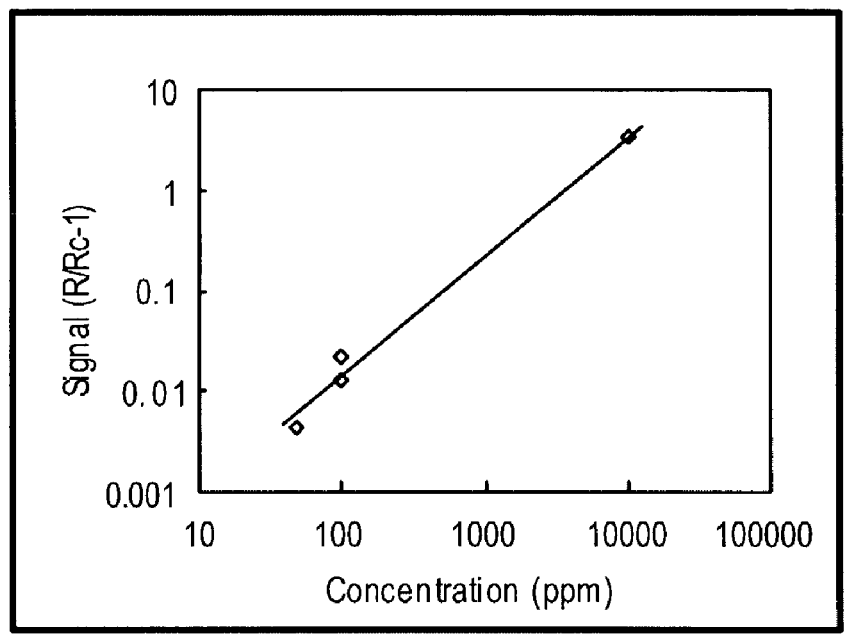
FIG. 9 is a graph of the response signal from the conducting polymer (CP) sensor element as a function of the ammonia concentration in gas phase.

FIG. 9 is a graph of the signal response of the sensor element CP as a function of the ammonia vapor concentration. It can be observed that the signal is proportional to the ammonia vapor concentration in the range from 50 to 10,000 ppm.

Example 6

Response of an Array to Multiple Analytes

An array sensor (cf. Table II) was exposed to a mixture of 100 ppm ammonia in He and 50 ppm HCl in He (resulting in 50 ppm ammonia and 25 ppm HCl in He) at a flow rate of 20 mL/min. Table III lists the responses of the sensor chip to 100 ppm ammonia, 50 ppm HCl, and the mixture containing both analytes. Artificial neural network (ANN), a pattern recognition technique, was used for the identification of the mixture. A commercially available ANN program (MatLab) was used to train the multilayer feedforward network. Data sets for 100 ppm ammonia and 50 ppm HCl were used for the training. The ANN approach was able to identify the vapor as a mixture of HCl and ammonia. Accuracy in the vapor composition can be achieved by providing more data sets for the ANN training.

TABLE III

Responses of an array sensor to ammonia, HCl, and their 1:1 mixture.

| Analyte | CP only | CP #18 | CP #8 | CP #30 | CP #23 | CP #36 |
|---|---|---|---|---|---|---|
| 100 ppm ammonia | 0.0343 | 0.0318 | 0.0382 | 0.0071 | 0.0126 | 0.0182 |
| 50 ppm HCl | 0.0040 | 0.0041 | 0.0084 | 0.0024 | 0.0090 | 0.0063 |
| Mixture | 0.0141 | 0.0199 | 0.0204 | 0.0054 | 0.0247 | 0.0150 |

Example 7

Signal Enhancement by the use of a Pre-Concentrator

Figure 10:
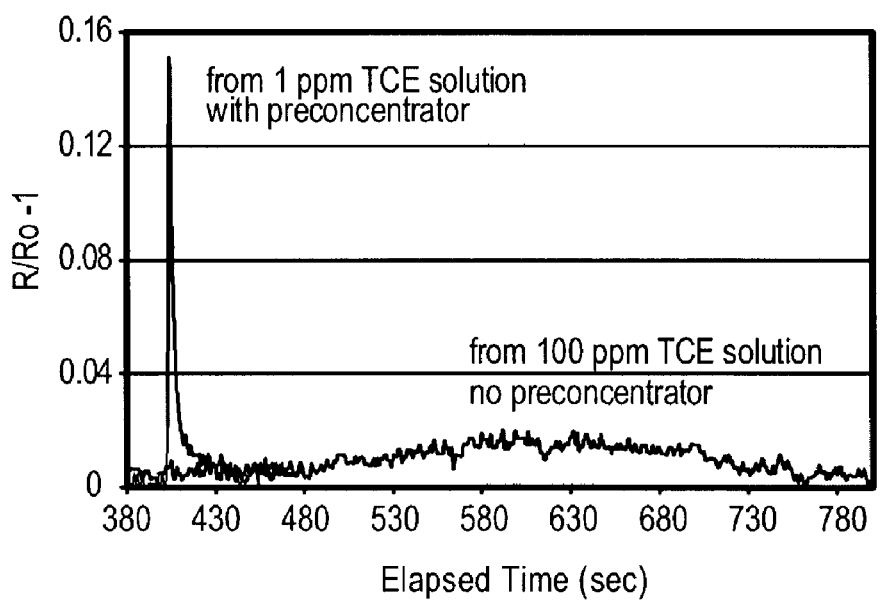
FIG. 10 is a graph of the response from a single conducting polymer sensor element when exposed to TCE gas samples with and without preconcentration.

The signal enhancement achieved by the use of a pre-concentrator is demonstrated in this example. Ambient air was bubbled at 150 mL/min through a solution containing 100 ppm TCE and then to the sensor chamber (the "flow-through sample"). In another experiment, ambient air was bubble at 150 mL/min through a solution containing 1 ppm TCE, and then through a pre-concentrator for VOCs (Carbotrap™ 302 Dynatherm ACEM, Supelco, Bellefonte, Pa.). The TCE was desorbed from the pre-concentrator by heating it at 250° C. and flowing ambient air at 25 mL/min through it (the "pre-concentrated sample"). FIG. 10 is a graph of the response from a single conducting polymer sensor element when exposed to the gas samples mentioned above with and without preconcentration. The flow-through sample produces a much broader signal with a small peak height, whereas the pre-concentrated sample produced a sharp, tall peak. This data shows that a pre-concentrator is capable of increasing the detection limit by a factor of 1200 while reducing the dispersion to 2.5 seconds FWHM.

As used herein, the term "electronic circuit" includes a signal processor, and the term "signal processor" includes digital signal processors, microprocessors, microcontrollers, and field programmable gate arrays.

It will be understood that certain combinations and sub-combinations of the invention are of utility and may be employed without reference to other features in sub-combinations. This is contemplated by and is within the scope of the present invention. As many possible embodiments may be made of this invention without departing from the spirit and scope thereof, it is to be understood that all matters hereinabove set forth or shown in the accompanying drawings are to be interpreted as illustrative and not in a limiting sense.

What is claimed is:

1. A device for detecting the presence of an analyte in a fluid comprising:
   a plurality of sensor elements, each sensor element comprising a pair of electrodes and an electronically conducting polymer composition in contact between the pair of electrodes, wherein each polymer composition is different; and
   an electronic circuit comprising a dynamic bridge, the electronic circuit being coupled to the pairs of electrodes for measuring a parameter of each polymer composition, wherein the dynamic bridge comprises a first resistance input from a constant current source in electrical communication with the sensor elements and a second resistance input from a microcontroller for balancing the dynamic bridge by adjusting the second resistance input to equal the first resistance input, wherein the constant current source is not in direct electrical communication with the second resistance input.

2. The device of claim 1, wherein the parameter is selected from an electrical parameter, a chemical parameter or combinations thereof.

3. The device of claim 1, wherein the parameter is an electrical parameter.

4. The device of claim 1, wherein the parameter is electrical resistance.

5. The device of claim 4, wherein the electronic circuit comprises a signal processor and a memory device associated with the signal processor, the memory device having stored information identifying the analyte by the amount of the electronic resistance measured at one or more of the sensor elements.

6. The device of claim 5, wherein the analyte is identified by changes in the electronic resistance upon exposure to the analyte.

7. The device of claim 1, further comprising:
   a chamber containing the plurality of sensor elements; and
   a channel in fluid communication with the chamber for delivering an analyte-containing fluid into contact with a surface of each polymer composition.

8. The device of claim 7, wherein the chamber is made of a material with substantially no absorption of organic and inorganic vapors.

9. The device of claim 7, wherein the chamber is made of titanium.

10. The device of claim 7, further comprising:
    a heater and thermocouple in thermal communication with the chamber.

11. The device of claim 7, wherein the chamber is sealed.

12. The device of claim 7, wherein the chamber has a dead volume of less than 10 milliliters.

13. The device of claim 7, wherein the chamber has a dead volume of less than 5 mL.

14. The device of claim 7, wherein the chamber has a dead volume of less that 0.5 mL.

15. The device of claim 1, wherein two or more of the sensor elements have an electronically conducting polymer composition comprising an electronically nonconducting organic polymer.

16. The device of claim 1, further comprising:
    a nonconductive substrate upon which the electrode pairs are disposed.

17. The device of claim 16, wherein the nonconductive substrate is an alumina chip.

18. The device of claim 16, wherein the nonconductive substrate is a printed circuit board.

19. The device of claim 1, wherein the sensor elements are formed on one or more substrates.

20. The device of claim 1, wherein each pair of electrodes are interdigitated electrodes.

21. The device of claim 1, further comprising:
a computer in electronic communication with the electronic circuit.

22. The device of claim 1, further comprising:
means for identifying the analyte by the measured parameter.

23. The device of claim 1, further comprising:
a computer in electronic communication with the electronic circuit for quantifying the concentration of the analyte.

24. The device of claim 23, further comprising:
a memory device associated with the computer, the memory device having stored information identifying the concentration of the analyte by the amount of the electronic parameter measured at one or more of the sensor elements.

25. The device of claim 1, wherein the analyte is an organic molecule.

26. The device of claim 25, wherein the organic molecule is a volatile organic carbon.

27. The device of claim 25, wherein the organic molecule is a semi-volatile organic carbon.

28. The device of claim 1, wherein the analyte is a toxic industrial material.

29. The device of claim 1, wherein the analyte is a chemical warfare agent.

30. The device of claim 1, wherein the analyte is an odor.

31. The device of claim 1, wherein the analyte is present in a gas or a liquid.

32. The device of claim 1, wherein the electronically conducting polymer composition comprises a polymer selected from polypyrrole, polyaniline, thiophene, methylopyrrole and derivatives or mixtures thereof.

33. The device of claim 1, wherein the electronically conducting polymer composition comprises a dopant selected from p-toluenesulfonic acid monohydrate (pTSA), 1-octanesulfonic acid sodium salt (OSA), camphorsulfonic acid (CSA), anthraquinone-2-sulfonic acid sodium salt (ASA), lithium perchlorate (PER), 4-octylbenzenesulfonic acid sodium salt (OBS), 3-nitrobenzenesulfonic acid sodium salt (NBS) or mixtures thereof.

34. The device of claim 1, wherein the electronically conducting polymer composition comprises a dopant selected from camphorsulfonic acid (CSA), p-toluenesulfonic acid monohydrate (pTSA) or mixtures thereof.

35. The device of claim 1, wherein the electronically conducting polymer composition comprises an organic polymer selected from poly acetal resin, polyacrylamide, polyacrylic acid, polyacrylonitrile/butadiene/styrene, polybutanediol terephthalate, poly-n-butyl methacrylate, poly-iso-butyl methacrylate, poly-n-butyl methacrylate/iso-butyl methacrylate, poly caprolactam, poly caprolactone, polycarbonate bisphenol A, polyethylene, polyethylene/acrylic acid, polyethylene/maleic anhydride, polyethylene oxide, polyethylene vinyl acetate, polyethylmethacrylate, polyhexamethylene adipamide, polyhexamethylene dodecanediamide, polyhexamethylene sebacamide, polylaurolactam, polymethylmethacrylate, poly-alpha-methylstyrene, polypropylene, chlorinated polypropylene, polystyrene, polystyrene allyl alcohol, polystyrene/maleic anhydride, polysulfone, polytetrafluoroethylene, poly vinyl acetate, poly vinyl alcohol, poly vinyl butyral, poly vinyl chloride, poly-4-vinylphenol, polyvinylidene chloride/acrylonitrile, polyvinylidene chloride/vinyl chloride, polyvinylidene fluoride, poly vinyl methyl ether/maleic anhydride, poly N-vinylpyrrolidone or mixtures thereof.

36. The device of claim 1, wherein the electronic circuit can measure electrical resistance variations as small as $\frac{1}{4}\Omega$ in a sensor element having an electrical resistance as large as 100 M$\Omega$.

37. The device of claim 1, wherein the electronic circuit can measure electrical resistance variations as small as $\frac{1}{4}\Omega$ in a sensor element having an electrical resistance as large as 1 M$\Omega$.

38. The device of claim 1, wherein the second resistance input from the microcontroller further comprises:
a digital to analogue converter that receives an input signal from the microcontroller and sends an output signal as the second resistance input.

39. The device of claim 1, wherein the dynamic bridge further comprises:
an amplifier having the first resistance input from a constant current source in electrical communication with the sensor elements and the second resistance input from a D/A converter, wherein a digital output from the microcontroller is converted by the D/A converter to the second resistance input; and
an analogue output from the amplifier converted by an A/D converter to a digital input to the microcontroller, wherein the microcontroller balances the dynamic bridge by adjusting the second resistance input to equal the first resistance input.

* * * * *